United States Patent [19]
Nandagiri et al.

[11] Patent Number: 5,362,486
[45] Date of Patent: Nov. 8, 1994

[54] IN-SITU POLYMERIZATION OF OLIGOMERS ONTO HAIR

[75] Inventors: Arun Nandagiri, Libertyville; Jacqueline Hutter, Chicago; Ramiro Galleguillos, Glendale Heights, all of Ill.

[73] Assignee: Helene Curtis, Inc., Chicago, Ill.

[21] Appl. No.: 866,844

[22] Filed: Apr. 10, 1992

[51] Int. Cl.$^5$ .................. A61K 7/11; A61K 31/765; C08G 18/04; C08G 18/10
[52] U.S. Cl. .................................. 424/71; 424/47; 424/DIG. 1; 424/DIG. 2; 424/78.17; 525/28; 525/452
[58] Field of Search .............. 424/71, 47, 70, DIG. 1, 424/DIG. 2; 528/85; 523/212; 525/7, 28

[56] References Cited

U.S. PATENT DOCUMENTS

| | | | |
|---|---|---|---|
| 3,472,604 | 10/1969 | Dasher et al. | 8/10.2 |
| 3,633,591 | 1/1972 | Anzuino | 132/7 |
| 3,634,022 | 1/1972 | Robbins et al. | 8/127.51 |
| 3,645,781 | 2/1972 | Brown | 428/270 |
| 3,676,550 | 7/1972 | Anzuino | 424/71 |
| 3,801,272 | 4/1974 | Wagner et al. | 528/85 |
| 3,850,178 | 11/1974 | Schoenholz | 132/7 |
| 4,036,241 | 7/1977 | Karg et al. | 132/7 |
| 4,254,002 | 3/1981 | Speiling et al. | 525/7 |
| 4,278,659 | 7/1981 | Breuer | 424/71 |
| 4,309,526 | 1/1982 | Baccei | 528/75 |
| 4,551,486 | 11/1985 | Tateosian et al. | 523/212 |
| 4,588,760 | 5/1986 | Jachowicz et al. | 524/12 |
| 4,682,612 | 7/1987 | Giuliano | 132/73 |
| 4,704,272 | 11/1987 | Oh et al. | 424/70 |
| 4,741,855 | 5/1988 | Grote et al. | 252/142 |
| 4,766,005 | 8/1988 | Montgomery et al. | 424/70 |
| 4,788,006 | 11/1988 | Bolich, Jr. et al. | 252/550 |
| 4,789,720 | 12/1988 | Teffenhart | 528/76 |
| 4,798,876 | 1/1989 | Gould et al. | 525/457 |
| 4,810,582 | 3/1989 | Gould et al. | 428/423.1 |
| 4,902,499 | 2/1990 | Bolish, Jr. et al. | 424/47 |
| 4,960,588 | 10/1990 | Hoshowski et al. | 424/71 |
| 5,085,859 | 2/1992 | Halloran et al. | 424/DIG. 2 |

FOREIGN PATENT DOCUMENTS

| | | | |
|---|---|---|---|
| 0410393A2 | 1/1991 | European Pat. Off. | C08L 83/04 |
| 0473039A1 | 3/1992 | European Pat. Off. | A61K 7/11 |

OTHER PUBLICATIONS

Brendley and Bakule, "Chemistry of Acrylic Resins for Coatings," *Applied Polymer Science*, pp. 1050-1052, American Chemical Society, 1985.

(List continued on next page.)

*Primary Examiner*—Edward J. Werman
*Attorney, Agent, or Firm*—Marshall, O'Toole, Gerstein, Murray & Borun

[57] ABSTRACT

An aqueous, alcoholic or hydroalcholic composition containing one or more oligomers or prepolymers that are polymerized in-situ, while the oligomer(s) is in contact with the hair, for in-situ formation (polymerization) of a polymer. The oligomer compositions contain essentially no toxic, hazardous or harmful monomer(s), such as resorcinol. In-situ polymerization provides substantially increased body to the hair; provides better, more continuous films of polymer into and onto the hair; provides a polymer coating with less flaking; will provide a more complete bond to adjacent hair shafts and to each individual hair shaft; better protects the hair against uptake of humidity; strengthens damaged hair; resists removal through at least three shampoos; are useful together with permanent wave reducing and oxidizing agents to make permanent waves more durable; prevents leach out of hair colors; provides for higher loading of polymer into and onto the hair and, therefore, better set retention; and provides a more durable set retention that also protects the hair against thermal damage and better resists hair uptake of atmospheric contaminants. When the polymerization of the oligomer or prepolymer results in a thermoplastic polymer having a glass transition temperature ($T_g$) less than about 120° C., the polymer can be repeatedly heated and cooled to reset the hair many times to reconfigure the hair without degrading the polymer.

20 Claims, No Drawings

OTHER PUBLICATIONS

Lai and Baccei, "Synthesis and Structure-Property Relationships of UV-Curable Urethane Prepolymers with Hard-Soft Hard Blocks," *J. Applied Polymer Science*, vol. 42, pp. 2039-2044 (1991).

Zviak, *The Science of Hair Care*, pp. 149-181, Marcel Dekker, Inc. 1986.

Makinson, *Shrinkproofing of Wool*, pp. 280-282, Marcel Dekker, Inc. 1979.

Jones, Leeder, and Wemyss, "The Wrinkling Behaviour of Wool Fabrics: The Effect of Annealing and Cross-Linking," *J. Textile Institute*, vol. 63, pp. 135-141, 1972.

Feldtman and Fleischfresser, "Permanent-Press Effects in Wool Part IX: Stabilizing Set with Reactive Pre-Formed Polymers," *J. Textile Institute*, vol. 62, pp. 471-481, 1971.

Robbins, *Chemical and Physical Behavior of Human Hair*, 2nd Ed., pp. 196-224, Springer-Verlag, 1988.

Matsumoto and Oiwa, "Glycol Bis(allyl Phthalates) as Cocross-linkers for Diallyl Phthalate Resins," *Reactive Oligomers*, pp. 225-235, American Chemical Society, 1985.

Sperling, Mason, and Jordhamo, "Special Functional Triglyceride Oils as Reactive Oligomers for Simultaneous Interpenetrating Networks," *Reactive Oligomers*, pp. 237-249, American Chemical Society, 1985.

Robbins, et al., "Polymerization into Human Hair," *J. Soc. Cosmet. Chem.*, vol. 25, pp. 407-421, 1974.

Wolfram, "Modification of Hair by Internal Deposition of Polymers," *J. Soc. Cosmet. Chem.*, vol. 20, pp. 539-553, 1969.

IN-SITU POLYMERIZATION OF OLIGOMERS ONTO HAIR

FIELD OF THE INVENTION

The present invention is directed to an aqueous and/or alcoholic composition, or a composition containing other cosmetically acceptable solvents, containing a polymerizable oligomer that is applied onto hair to modify one or more cosmetic properties of the hair. The oligomer is polymerized, in-situ, while in contact with the hair to modify at least one hair property, such as body, conditioning, shine, set retention, combability, or the like. The oligomer can be polymerized, in-situ, while in contact with hair in any known manner, such as by including an initiator, e.g., a heat-activated initiator, or a polymerization catalyst in the oligomer composition and processing the composition, such as by heating the composition with a hair blow dryer, or other heating means or by use of an accelerator or catalyst, or the like.

BACKGROUND OF THE INVENTION AND PRIOR ART

Normal hair can be so fine and limp, and so lacking in body that the hair does not hold a hair set well. Furthermore, the hair can become even less bodied and can be weakened further as a result of being subjected to chemically active hair treatments, such as permanent waves and tints. Additionally, hair can be weakened even further by other contributing factors, such as bleaching by sun exposure and/or chlorinated swimming pool water.

Hair setting is basically the process of shaping wet hair by the steps of stretching the hair by curling the hair, fixing the hair in place by drying, then combing to give the finishing touches to provide the desired hair style. In particular, the setting of wet hair can be accomplished by making flat curls from strands of hair and fixing the curls with hairpins to produce "pin curls". Similarly, the wet hair can be set by using any of a variety of rollers or curlers to mechanically fix the hair. In either case, the winding of the wet hair is followed by drying, either by ambient air drying, electric drying or hot air drying.

The inherent problem encountered in hair setting is the natural tendency of the hair to return to its natural shape. For example, the set hair returns to its natural shape almost immediately if moistened. Likewise, high humidity conditions accelerate the tendency of the hair to return to its natural shape. Therefore, intensive efforts have been directed toward providing a hair set with sufficient holding power to maintain the designed hair style until at least the next shampoo, and, therefore, giving the hair set a degree of permanency.

Therefore, investigators have sought to delay the combined action of natural forces and moisture that causes the hair to return to its original state by applying solutions containing naturally-occurring or synthetic polymers after the hair is shaped into a desired configuration. When applied to the shaped hair from aqueous or aqueous/alcoholic solutions (setting lotions), the polymers leave a film on the hair, after drying, to help maintain the hair in the previously shaped configuration. The polymeric film promotes cohesion and gives stability to the hair set to maintain the hold of the hair set. The principal objective of a setting lotion is to cover the previously styled hair with an invisible polymeric film that will give the styled hair a degree of rigidity and protect the hair style against wind and humidity.

Hair spray products act in a similar manner. The hair spray products are applied to wet and/or dry hair and contain a polymer, or mixtures of polymers, that remain fixed on the previously styled hair and affect the hair in various ways. For example, a "mechanical" effect is exerted on each individual hair. The film-forming polymers are used to provide a flexible sheath of polymeric film on the shaped hair after drying and, therefore, for mechanical reasons, retard the return of each individual hair to its natural shape. In addition, the polymeric film provides an overall stiffening of the hair and the hair strands are welded together, and the final hair style has better cohesion, therefore resisting the natural forces that return the hair to its natural shape. Finally, the polymeric film protects the hair from humidity. The ability of the polymeric film to attract and absorb water is preferably minimal, such that the polymeric film retards moisture uptake by hair and retards the return of the hair to the natural configuration.

The general principles of hair setting are thoroughly discussed by C. Zviak, in The Science of Hair Care, Marcel Dekker, pp. 149–181 (1986). Zviak reviews both the polymers used in hair setting products and the formulation principles used to produce a hair set product that provides such beneficial hair set properties as improved hair style hold, easy application and combing, quick drying and non-stickiness, good hair body and bounce, increased hair volume and gloss, and hydrophobicity.

The prior art reveals that nonionic, cationic and anionic polymers have been used in hair set products, with the anionic polymers providing the best hair set results. However, anionic polymers also have disadvantages, such as high water-solubility and, therefore, low hydrophobicity, and low substantivity to hair fibers, therefore, easy elimination from the hair by combing and brushing. As a result, investigators have continued to search for compounds and compositions that provide the primary benefit of an improved durability of the hair set. As previously mentioned, to overcome some of the inherent disadvantages of the polymers utilized to set the hair, hair set products are made available in diversified forms in an attempt to minimize the drawbacks of the particular polymer used in the formulation. For example, hair set products are available as plasticizing lotions, plasticizing gels, aerosol foams, all-purpose lotions, hair sprays, and holding lotions.

Others have attempted to polymerize monomers, in-situ, while in contact with hair, as discussed in "Polymerization Into Human Hair", Robbins, et al., Journal of Society of Cosmetic Chemists, Vol. 25, pp. 407–421, August, 1974; "Modification of Hair By Internal Deposition Of Polymers", Wolfram, Journal of Society of Cosmetic Chemists, Vol. 20, pp. 539–553, Aug. 19, 1969; and U.S. Pat. Nos. 3,472,604; 3,676,550; 3,634,022 and 4,588,760. The monomers have been problematic due to the tendency of the monomeric materials to be irritating and/or harmful to the hair and/or skin of the user, particularly absorption of harmful monomers into the skin of the user, and of the harsh feel left in the hair or hair discoloration. Further, the reduction of hair prior to treatment generally is necessary and causes additional damage to the hair.

A major deficiency in prior art polymer hair treatments is the lack of durability of these treatments, usually washing out after one or two shampoos. The in-situ polymerization in accordance with the present invention provides a desirable polymer that lasts at least through three shampoos. While other researchers have attempted to improve the durability of polymer treatments by forming the polymer in-situ, the main drawback to these previous treatments was that toxic and/or irritating monomeric species were used. One patent, Breuer U.S. Pat. No. 4,278,659 discloses the application of an oligomer formed by the condensation reaction of glyceraldehyde and resorcinol heated together in the presence of boric acid or silicic acid that only partially polymerizes the monomers. One of the problems with the application of the oligomeric composition disclosed in U.S. Pat. No. 4,278,659 is that the pH of the composition must be at or below about 1.6 to achieve the polymerization of the monomers due to the necessity of the acid addition, requiring later alkali addition for raising the pH to an acceptable level before the composition can be safely applied to the hair. Another problem with the oligomeric composition disclosed in U.S. Pat. No. 4,278,659 is that a substantial quantity of monomer that has not polymerized is left in the composition. Resorcinol becomes pink upon exposure to light and air and significant absorption into the skin through the scalp or hands can cause health problems, or even death. Accordingly, until the present invention, there has been no safe and effective oligomeric hair care composition or method of applying an oligomeric composition to hair and further polymerizing the oligomer while in contact with the hair.

U.S. Pat. No. 4,682,612 discloses oligomers such as urethane-acrylates that are photoinitiated in the formation of artificial nails as long as positive benefits are conferred to the hair. Any of the oligomers disclosed in U.S. Pat. No. 4,682,612 are useful in accordance with the present invention so long as the monomer is not harmful to the skin and the U.S. Pat. No. 4,682,616 is hereby incorporated by reference.

In accordance with the present invention, a new and improved aqueous, alcoholic or hydroalcoholic composition, or compositions containing other cosmetically acceptable solvents, and methods have been found wherein a safe polymerizable oligomer or prepolymer composition having essentially no irritating or harmful monomers and/or oligomeric materials, is applied to wet or dry hair and, thereafter, the hair is processed to polymerize the oligomer, in-situ, while in contact with the hair, to further polymerize the oligomer(s) or prepolymer(s). The oligomer(s) or prepolymer(s) are polymerized in-situ, e.g., with a thermal appliance, such as a blow dryer or a curling iron, and/or by including a polymerization accelerator or polymerization catalyst in the composition, or in a separate composition. Polymerization, in-situ, without the presence of toxic, hazardous or harmful monomer(s) or oligomer(s), has substantial advantages over application of a completely polymerized polymer or polymerization of an oligomer mixed with toxic or hazardous monomer(s) since in-situ polymerization enables the oligomer to be in contact with the hair during the various polymerization stages for better chemical attachment to the hair while minimizing the possibility of the absorption of harmful monomers into the user's skin. Further, in-situ polymerization provides substantially increased body to the hair; provides better uptake of polymer onto the hair; provides a polymer coating with less flaking; can provide a more complete attachment of the resulting polymer to the hair; better protects the hair against uptake of humidity; strengthens damaged hair; resists removal through at least three shampoos; are useful to make permanent waves more durable without reducing agent odor; prevents leach out of hair colors; can provide for higher loading of polymer into and onto the hair and, therefore, better set retention; protects the hair against thermal damage and better resists hair uptake of atmospheric contaminants.

SUMMARY OF THE INVENTION

In brief, the present invention is directed to an aqueous, alcoholic or hydroalcoholic composition, or compositions containing any cosmetically acceptable solvent, containing one or more oligomers or prepolymers that are polymerized in-situ, while the oligomer(s) is in contact with the hair, for in-situ formation (polymerization) of a polymer. The oligomer compositions of the present invention contain essentially no toxic, hazardous, irritating or harmful monomer(s) or oligomer(s) such as resorcinol. The oligomer compositions can be provided in the form of a mousse, lotion, emulsion, paste, liquid, foam or gel composition. The present invention further is directed to a method of applying the oligomer composition to hair, and thereafter polymerizing the oligomer, in-situ, to beneficially alter one or more surface properties of the hair, such as increased body, increased shine, better set retention, better combability, better conditioning and to impart durability to all of these properties. After application of the oligomer composition to wet or dry hair, before or after styling, the hair then is treated in such a manner to polymerize the oligomer(s) or prepolymer(s) in the composition.

The composition of the present invention includes a water-soluble or water-dispersible or solvent-soluble or solvent-dispersible oligomer or prepolymer without any toxic monomer(s), and, after polymerization, in-situ, becomes a polymer or resin that imparts substantially increased body to the hair and, depending upon the particular oligomer, may also impart one or more other conditioning properties, such as a durable shine or combability; resistance to uptake of humidity and atmospheric contaminants; resistance to hair color loss and/or durable set retention. The oligomer can be applied in any manner, such as from a lotion, gel, mousse, emulsion, or the like.

The compositions and methods of the present invention can be more effective than application of similar resins that are completely polymerized prior to application to the hair. The amount of water and/or alcohol or other solvent carrier(s) in the compositions of the present invention can be in the range of about 0.5% to about 99.5% by weight of the composition; alcohol or other solvents may be included in an amount of 0% to about 99.5% by weight.

Accordingly, one aspect of the present invention is to provide a new and improved hair treating composition containing a set retention oligomer (a prepolymer or oligomer that, after further polymerization while in contact with human hairs will aid in retaining the hair in a desired configuration), and method, that can be applied to the hair from an aqueous and/or solvent, e.g., alcoholic, composition in the form of a mousse, lotion, emulsion, foam or gel for providing improved body, shine, combability and/or other mechanical or surface improvement to the hair after the oligomer or prepolymer has been further polymerized while in contact with the hair.

Another aspect of the present invention is to provide an aqueous, solvent, e.g., alcoholic, hydroalcoholic or other cosmetically acceptable solvent, hair bodifying and/or styling aid composition, and method, in the form of a mousse, emulsion, lotion, foam or gel, that is activated by heat, actinic light, e.g., ultraviolet light, EB radiation and/or activator and/or catalyst and polymerized, after application to the hair, to form a set-retaining polymer while in contact with the hair, without the presence of a toxic, hazardous or harmful monomer or oligomer in the composition.

In one embodiment, the oligomer or prepolymer is polymerized in-situ to form a thermoplastic set-retaining polymer so that the configuration of the hair can be repeatedly changed by softening the thermoplastic polymer, e.g., using thermal appliances, such as curling irons, hot crimpers, heated rollers, hair dryers or other types of hair heating devices used for drying or shaping of hair to heat the polymer above its glass transition temperature ($T_g$), and then cooling the hair below the $T_g$ to set the hair in the new configuration, wherein the composition includes a thermoplastic oligomer capable of hardening rapidly after polymerization, while the hair is in a desired configuration, upon removal of the thermal appliance from the hair, to provide a durable hair set capable of repeated reconfiguration without substantial set loss.

Another aspect of the present invention is to provide a safe oligomer composition in the form of a mousse, foam, lotion or gel that includes water and/or or other cosmetically acceptable solvents, e.g., alcohol in an amount of about 1% to about 99.5% by weight of the composition; and a thermoplastic oligomer that is solubilized or dispersed in the water and/or solvent carrier in an amount of about 0.1% to about 99.5%.

The above and other aspects and advantages of the present invention will become more apparent from the following detailed description of the preferred embodiments.

DETAILED DESCRIPTION OF THE PREFERRED EMBODIMENTS

The oligomers or prepolymers useful in the compositions and methods of the present invention are polymerizable oligomers or prepolymers that are polymerizable while in contact with human hair resulting in polymers that improve one or more mechanical or surface properties of the hair.

The preferred oligomers are reactive urethanes and urethane-acrylate oligomers, particularly the urethane-acrylate oligomers. Urethane oligomers and urethane-acrylate oligomers are commercially available as radiation-curable prepolymers. The urethane-acrylates, in particular, are preferred and are prepared by reacting one or more polyols with one or more disocyanates and end-capping with a hydroxyalkyl acrylate. These urethane-acrylate prepolymers result in crystal clear polymers and can be prepared with mixed soft and hard segments to provide the desired mechanical properties, as disclosed in Lai and Baccei's article, "Synthesis and Structure—Property Relationships of UV-Curable Urethane Prepolymers With Hard-Soft-Hard Blocks", Journal of Applied Polymer Science, Vol. 42, pp. 2039-2044 (1991) and U.S. Pat. No. 4,309,526, both hereby incorporated by reference. The urethane-acrylate prepolymers that are end-capped with acrylate groups, are readily polymerized, in-situ, with an initiator, such as benzoyl proxide or benzoin methyl ether, with ultraviolet light. Dried urethane prepolymer films can be provided on the hair and the films polymerized with ultraviolet light.

The reaction between hydroxyl and isocyanate groups proceeds efficiently at low temperatures without the evolution of volatile by-products. One of the simplest radiation curable urethane-acrylate prepolymers is formed with the end-capping reaction of 2 moles of an hydroxy acrylate, for example, hydroxy ethyl acrylate or hydroxy propyl acrylate with 1 mole of a diisocyanate. Such a product will be highly viscous and produce cured films which are very hard and inflexible but also highly chemical resistant.

Two main classes of isocyanates are available: aromatic, e.g., toluene diisocyanate, and aliphatic, e.g., isophorone diisocyanate. Aromatic isocyanates result in higher viscosity urethanes. An improvement in performance and processability is achieved by incorporating an aliphatic-based isocyanate.

The opportunities for tailor making urethane-acrylates with different characteristics and levels of performance include, e.g., improvement in flexibility by chain extension using long chain ($C_{12}$–$C_{22}$), diols, polyethers, polyesters or polycarbonates to produce a higher molecular weight isocyanate functional prepolymer which is subsequently capped by a hydroxy acrylate monomer.

Some of the useful radiation-curable urethane-acrylate oligomers can be obtained commercially from Henkel Corporation, Ambler, Pa.—particularly, the aliphatic urethane-acrylates, e.g., PHOTOMER 6008, 6008-T; 6010; 6019; 6022; 6060; 6110; 6160; 6184; 6210; 6230; and 6264. Other resilient to hard aliphatic urethane-acrylate oligomers can be obtained from SARTOMER Corporation as Sartomer CN 961 (resilient); CN 964 (resilient); CN 960 (hard); CN 962 (flexible); CN 965 (flexible); and aromatic urethane-acrylate oligomers, also can be obtained from SARTOMER as CN 970 (hard); CN 971 (resilient); and CN 972 (flexible). As an example of a commercially available urethane oligomer, mention may be made of "Uvithane" (trademark of Thiokol Speciality Chemical Division).

The oligomers that may be used include, for example, the commercially available low molecular weight oligomers, e.g., urethanes such as those having a molecular weight ranging from about 600 to about 8,000 or 10,000, and particularly those containing no reactive isocyanate groups; the epoxies; and the polymethacrylates. The preferred oligomers have a degree of polymerization (dp) in the range of about 2 to about 200. The urethanes, especially the acrylated urethanes, being particularly preferred. Other oligomers that are particularly useful include any prepolymer that is hydroxy terminated or amino terminated. Other prepolymers which are particularly useful include thiol containing material; crosslinkable polydimethylsiloxanes; or crosslinking polyacrylates.

Useful photoinitiators are also well known in the art and include peroxo and diazo compounds, and the aromatic ketones such as benzophenone.

Also useful are the allyl thermosetting oligomers, particularly the glycol bis(allyl phthalate) and the glycol bis(diallyl phthalate) and glycol bis(isophthalate) oligomers to produce a diallyl phthalate polymer, polymerized in contact with the hair, having improved flexibility. Also useful are functional triglyceride oils, such as corn oil and tallow oil and castor oil, having functionalities including hydroxy groups and epoxy or oxirane groups. Triglyceride oils have glycerol as a backbone and three fatty acids as side chains. These oils react directly with many chemical reagents yielding polyurethane or polyester polymer networks. Castor oil contains three hydroxyl groups, one on each acid residue:

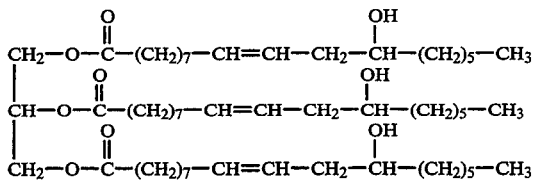

Other suitable triglyceride oils include vernonia oil, which is a triglyceride oil that naturally contains 80% epoxy groups on an acid residue basis, and ordinary triglyceride oils, such as linseed oil, whose double bonds are epoxidized.

Another oil of interest is lesquerella oil, which comes from a desert wild flower native to Arizona, and known locally as pop weeds or bladder pods. This oil is similar to castor oil, except that it has two more —$CH_2$— groups in between the glycerol and hydroxyl groups. Consequently, its polymers tend to have slightly lower glass transition temperatures.

In addition to esterification, these oils can also be reacted with isocyanates to make polyurethanes. Some of the most interesting oligomers consist of mixed ester-urethane compositions, wherein the ester portion is made before gelation and wherein the water can be evaporated easily, and the urethane component is added as a type of postcure.

An interpenetrating polymer network, IPN, can be defined as a combination of two polymers in network form, at least one of which was polymerized or synthesized in the presence of the other. These networks are synthesized sequentially in time. A simultaneous interpenetrating network, SIN, is an IPN in which both networks are synthesized simultaneously in time, or both monomers or prepolymers mixed prior to gelation. The two polymerizations are independent and non-interfering in an SIN, so that grating or internetwork crosslinking is minimized.

In the simultaneous interpenetrating networks (SIN), the two reactions are run simultaneously. One reaction, for example, can be a polyesterification or a polyurethane stepwise reaction.

Of particular interest are water-soluble polycarbamoyl sulfonate oligomers having a degree of polymerization of 2 to about 200. Such oligomers are commercially available as SYNTHAPPRET BAP from Miles of Pittsburgh, Pa. The polycarbamoyl sulfonates can be used together with other oligomers, such as the polyacrylates or while crosslinking a polydimethylsiloxane in-situ.

Other oligomers of particular interest are the self-crosslinking vinyl polyacrylates, such as the PRIMAL Series of Oligomers sold by Rohm and Haas of Philadelphia, Pa. Suitable prepolymers with thiol groups include the OLIGAN Series of prepolymers from Ciba-Geigy of Basel, Switzerland.

Acrylic (ethylenic) oligomers, having a degree of polymerization from about 2 to about 200, particularly about 2 to about 20, are suitable in accordance with the present invention.

The ethylenic oligomers are solubilized or dispersed in a suitable carrier, a crosslinking agent, and a thermal and/or redox initiator is separately added or activated with heat or light just prior to or just after hair contact. One or more emulsifying agents can be included in the oligomer composition, if necessary, to disperse a water or solvent-insoluble oligomer.

An acrylic (ethylenic) oligomer may be mixed with a polyvinyl monomer crosslinking agent in an aqueous or hydroalcoholic solution. The solution is subjected to a polymerization reaction and/or a crosslinking reaction by the addition of a polymerization initiator just prior to hair application or applied to the hair separately, and the polymerization reaction proceeds. The oligomer solution can be prepared easily by reacting an ethylenic prepolymer, with or without a crosslinking agent, in water or water and solvent, e.g., alcohol, to form an oligomer solution.

The polyvinyl monomer crosslinking agent should be miscible with or soluble in water, alcohol or other cosmetically acceptable solvent(s) so that the monomer will be uniformly dissolved or dispersed in the solution of the oligomer solution. Examples of such polyvinyl monomers include bisacrylamides such as N,N'-methylenebisacrylamide and N,N'-methylenebismethacrylamide; polyacrylic (or polymethacrylic) acid esters represented by the following formula (I); and diacrylamides. Among these especially preferable are N,N'-methylenebisacrylamide, N,N'-methylenebismethacrylamide and like bisacrylamides.

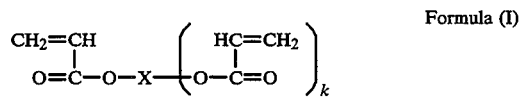

Formula (I)

wherein x is ethylene, propylene, trimethylene, hexamethylene, 2-hydroxypropylene, $(CH_2CH_2O)_nCH_2CH_2$— or

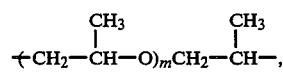

n and m are each an integer of from 5 to 40, and k is 1 or 2.

The compounds of the formula (I) are prepared by reacting polyols, such as ethylene glycol, propylene glycol, trimethylolpropane, 1,6-hexanediol, glycerin, pentaerythritol, polyethylene glycol and polypropylene glycol, with acrylic acid or methacrylic acid.

The compounds of the formula (II):

wherein l is 2 or 3.

are obtained by reacting polyalkylene polyamides, such as diethylenetriamine and triethylenetetramine, with acrylic acid.

The polyvinyl monomer crosslinking agent is used in an amount of about 0.001 to 2.0 wt. % of the amount of oligomers in the aqueous mixture. Preferably, the crosslinking agent is present in the aqueous solution in an amount of at least 0.2 wt. % based on the total weight of oligomers.

A reaction initiator can be added to the oligomer solution/dispersion just prior to use, or is applied to the hair from a separate application for polymerization and crosslinking, or activated with heat or light. Various polymerization initiators, such as peroxo or diazo compounds are usable which are known for use in preparing polyacrylates. Examples of useful initiators are redox initiators comprising a reducing agent, such as a sulfite or bisulfite of an alkali metal, ammonium sulfite or ammonium bisulfite, and an initiator, such as a persulfate of an alkali metal or ammonium persulfate, in combination with the reducing agent; azo and/or diazo initiators incuding azobis-isobutyronitrile, 4-t-butylazo-4'-cyanovaleric acid, 4,4'-azobis(4-cyanovaleric acid) and 2,2'-azobis(2-amidinopropane)-hydrochloric acid salt; and the like. These initiators can be used singly or in a suitable combination. Of these, especially preferable are a redox initiator composed of ammonium persulfate and sodium hydrogen-sulfite, and azo initiators such as azobisisobutyronitrile and 2,2'-azobis(2-amidinopropane)-hydrochloric acid. These initiators are advantageously used usually in the form of an aqueous solution but can be used as diluted with a suitable solvent. The initiator is used in a usual amount, i.e., in an amount, calculated as solids, of about 0.1 to about 10%, preferably about 0.5 to about 5%, of the combined weight of the oligomers. Depending on the amount and kind of the initiator, the initiator is usable together with isopropyl alcohol, alkylmercaptan or other chain transfer agents, in usual amounts of about 0.1% to about 5% by weight of the oligomers in the composition, to control the molecular weight of the polymer, e.g., polyacrylate to be obtained.

The polymerization reaction for polyacrylates is exothermic so that after initial heating, or by including a small amount of a thermal initiator, further heating should be unnecessary, but is useful to speed the polymerization reaction. With other oligomers, heating can be sustained to achieve evaporation of solvents from the reaction product.

In accordance with one embodiment, the oligomers or prepolymers, after in-situ polymerization, result in thermoplastic polymers that do not chemically degrade upon repeated heating and cooling. These polymers, after in-situ polymerization, therefore, are exceptionally suitable for thermo-styling of hair with curling irons, hot crimpers, rollers, and any other heating device used in hair styling. In this embodiment, shaping of the hair is best accomplished by first applying the oligomer composition to hair while wet, polymerizing the oligomer in-situ, while in contact with the hair, allowing the hair to dry, and then physically shaping the hair with the hot styling aid. The heat softens the resin, thereby allowing it to spread along the hair shaft and acquire the configuration of the hot styling aid. After removing the hot styling aid, the resin hardens on individual hair shafts, maintaining the hair in the shape imparted by the styling aid. Because of the thermal stability of the thermoplastic resins, the hair can be restyled at any time, adding a convenience which is not possible to obtain with conventional hair fixative resins.

In accordance with another important feature of the present invention, any ionizable metal salt, wherein the metal has a valence of at least II, can be included in the composition, in an amount of about 0.1% to about 10% based on the weight of oligomer(s) in the composition, for in-situ oligomer crosslinking, to improve durability of the mechanical or surface property improvement imparted to the hair by the oligomer. Hair treated with the oligomer compositions of the present invention adjusted to a pH above about 7.0, preferably above about 8.0, and containing an ionizable metal salt exhibits improved mechanical and surface properties, such as body and shine if the metal of the ionizable metal salt has a valence of at least II.

The oligomer can be crosslinked in-situ with polyvalent metal compounds such as those described in U.S. Pat. No. 3,850,178, hereby incorporated by reference. Other useful polyvalent metal compounds include those described in U.S. Pat. No. 4,036,241, at lower pH's, and this assignee's U.S. Pat. No. 4,960,588, both patents hereby incorporated by reference. A crosslinked polymer composition is obtained by first solubilizing or dispersing the resin in water and/or a solvent, such as ethanol, adding ammonium hydroxide to pH 9.0 or higher, and then adding potassium or ammonium alum. The composition then is applied onto the hair, the hair is allowed to dry, and the oligomer is polymerized and crosslinked in-situ while in contact with the hair.

The polydimethylsiloxanes are one example of a material that can be crosslinked in-situ. The amino and/or silanol functional polydimethylsiloxanes can be obtained from Dow Chemical and are particularly suitable. These materials can be crosslinked in-situ by including a standard amount up to about 1% by weight of a suitable catalyst together with the crosslinking agent.

It is preferred to keep the level of surfactants in the oligomer composition as low as possible (preferably less than about 5% by weight and, more preferably, less than about 3% by weight). Sandoperm FE or any other water-dispersible silicone, or other conditioning agent, can be added for conditioning benefits. Fragrance preferably is added last. Mousse compositions can be placed in a mousse can or bottle and charged with propellant. Propellants can be any of the gases known in the art. It is preferred to use dimethyl ether (DME) or blends of DME with a hydrocarbon gas.

In accordance with one embodiment, the oligomer or prepolymer composition of the present invention also optionally includes from about 0.1% to about 10%, particularly about 0.5% to about 10%, and preferably from about 1.0% to about 5.0%, by weight of a nonvolatile silicone compound or other conditioning agent(s), preferably a water-insoluble, emulsifiable conditioning agent. The preferred non-volatile silicone compound is a polydimethylsiloxane compound, such as a mixture, in about a 3:1 weight ratio, of a low molecular weight polydimethylsiloxane fluid and a higher molecular weight polydimethylsiloxane gum. The non-volatile polydimethylsiloxane compound is added to the composition of the present invention in an amount sufficient to provide improved combing and improved feel (softness) to the hair after shampooing. As referred to herein, "silicone gums" are those nonfunctional siloxanes having a viscosity of from about 5 to about 600,000 centistokes at 25° C. The so-called rigid silicones, as described in U.S. Pat. No. 4,902,499, herein incorporated by reference, having a viscosity above 600,000 centistokes at 20° C., e.g., 700,000 centistokes plus, and a weight average molecular weight of at least about 500,000 also are useful in accordance with the present invention.

As mentioned previously, the silicone materials may be used as prepolymers, as well as conditioning agents. This is not deleterious to the composition, however, since the silicones will be active participants in the in-situ polymerization making the conditioning benefits more long lasting.

Preferred silicone gums include linear and branched polydimethylsiloxanes, of the following general formula:

$(CH_3)_3SiO-[Si(CH_3)_2O]_n-Si(CH_3)_3$, wherein n is from about 2,000 to about 15,000, preferably from about 2,000 to about 7,000. Silicone gums useful in compositions of the present invention are available from a variety of commercial sources, including General Electric Company and Dow Corning.

Another particularly suitable conditioning agent that can be included in the oligomer or prepolymer composition of the present invention is a volatile hydrocarbon, such as a hydrocarbon including from about 10 to about 30 carbon atoms, that has sufficient volatility to slowly volatilize from the hair after application of the aerosol or non-aerosol styling aid composition. The volatile hydrocarbons provide essentially the same benefits as the silicone conditioning agents.

The preferred volatile hydrocarbon compound is an aliphatic hydrocarbon including from about 12 to about 24 carbon atoms, and having a boiling point in the range of from about 100° C. to about 300° C. Exemplary volatile hydrocarbons are depicted in general structural formula (I), wherein n ranges from 2 to 5,

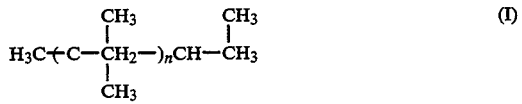

Examples of volatile hydrocarbons useful in the composition of the present invention are the commercially-available compounds PERMETHYL 99A and PERMETHYL 101A, corresponding to compounds of general structure (I) wherein n is 2 and 3, respectively, available from Permethyl Corporation, Frazer, Pa. A volatile hydrocarbon compound is useful in the composition of the present invention either alone, in combination with another volatile hydrocarbon, or in combination with a volatile silicone.

Examples of other suitable water-insoluble conditioning agents that can be incorporated into the styling aid composition of the present invention include the following: polysiloxane polyether copolymers; polysiloxane polydimethyl dimethylammonium acetate copolymers; acetylated lanolin alcohols; dimethyl dialkyl ammonium chlorides; modified alkyl dimethyl benzyl ammonium chlorides; lauryl dimethylamine oxide; stearyl dimethyl benzyl ammonium chloride; a lanolin-derived extract of sterol on sterol esters; lanolin alcohol concentrate; an isopropyl ester of lanolin fatty acids; sulfur rich amino acid concentrates; isopropyl ester of lanolin fatty acids; cetyl trimethyl ammonium chloride; oleyl dimethyl benzyl ammonium chloride; oleyl alcohol; stearyl alcohol; stearamidopropyl dimethyl myristyl acetate; a polyol fatty acid; a fatty amido amine; guar hydroxypropyltrimonium chloride; cetyl/stearyl alcohol; quaternized protein; keratin protein derivatives; isostearamidopropyl dimethylamine; stearamidopropyl dimethylamine; cetrimonium bromide; myrtrimonium bromide; stearalkonium chloride; cetyl trimethyl ammonium chloride; laurylpyridinium chloride; tris-(oligoxyethyl)alkyl ammonium phosphate; an aminofunctional silicone; lapyrium chloride; isopropyl ester of lanolic acids; ethoxylated (30) castor oil; acetylated lanolin alcohol; fatty alcohol fraction of lanolin; a mineral oil and lanolin alcohol mixture; high molecular weight esters of lanolin; quaternium-75; vinylpyrrolidone/dimethylaminoethylmethacrylate copolymer; alkyl trimethyl ammonium chloride; 5 mole ethylene oxide adduct of soya sterol; 10 mole ethylene oxide adduct of soya sterol; stearic acid ester of ethoxylated (20 mole) methyl glucoside; sodium salt of polyhydroxycarboxylic acid; hydroxylated lanolin; cocamidopropyl dimethylamine lactate; cocamidopropyl dimethylamine propionate; cocamidopropyl morpholine lactate; isostearamidopropyl dimethylamine lactate; isostearamidopropyl morpholine lactate; oleamidopropyl dimethylamine lactate; linoleamidopropyl dimethylamine lactate; stearamidopropyl dimethylamine lactate, ethylene glycol monostearate and propylene glycol mixture; stearamidopropyl dimethylamine lactate; acetamide MEA; lactamide MEA; stearamide MEA; behenalkonium chloride; behenyl trimethyl ammonium methosulfate and cetearyl alcohol mixture; cetearyl alcohol; isostearamidopropalkonium chloride; linoleamidopropalkonium chloride; oleyl dimethyl benzyl ammonium chloride; tallow imidazolinum methosulfate; stearyl trimonium methosulfate; mixed ethoxylated and propoxylated long chain alcohols; stearamidopropyl dimethylamine lactate; polonitomine oxide; oleamine oxide; stearamine oxide; soya ethyldimonium ethosulfate; hydroxypropyl bislauryl dimonium chloride; hydroxypropyl biscetyl dimonium chloride; hydroxypropyl bisstearyl dimonium chloride; hydroxypropyl bisbehenyl dimonium chloride; ricinolamidopropyl ethyldimonium ethosulfate; olealkonium chloride; stearalkonium chloride; N-(3-isostearamidopropyl)-N,N-dimethyl amino glycolate; N-(3-isostearamidopropyl)-N,N dimethyl amino gluconate; hydrolyzed animal keratin; ethyl hydrolyzed animal keratin; stearyl ammonium chloride; stearamidoethyl diethylamine; cocamidopropyl dimethylamine; lauramidopropyl dimethylamine; oleamidopropyl dimethylamine; palmitamidopropyl dimethylamine; stearamidopropyl dimethylamine lactate; avocado oil; sweet almond oil, grape seed oil; jojoba oil; apricot kernel oil; sesame oil; hybrid safflower oil; wheat germ oil; cocamidoamine lactate; ricinoleamido amine lactate; stearamido amine lactate; stearamido morpholine lactate; isostearamido amine lactate; isostearamido morpholine lactate; wheat germamido dimethylamine lactate; behenamidopropyl betaine; ricinoleamidopropyl betaine; wheat germamidopropyl dimethylamine oxide; disodium isostearaimido MEA sulfosuccinate; disodium oleamide PEG-2 sulfosuccinate; disodium oleamide MEA sulfosuccinate; disodium ricinoleyl MEA sulfosuccinate; disodium wheat germamido MEA sulfosuccinate; disodium wheat germamido PEG-2 sulfosuccinate; stearamido amine; stearamido morpholine; isostearamido amine; isostearamido morpholine; polyethylene glycol (400) mono and distearates; synthetic calcium silicate; isostearic alkanolamide; ethyl esters of hydrolyzed animal protein; blend of cetyl and stearyl alcohols with ethoxylated cetyl or stearyl alcohols; amido amines; polyamido amines; palmityl amido betaine; propoxylated (1-20 moles) lanolin alcohols; isostearamide DEA; and hydrolyzed collagen protein. The presence of oligomer-reactive group(s) on any of these conditioning agents allows the conditioning agent to react with the oligomer during in-situ polymerization for incorporation into the polymer.

When one or more of these water-insoluble conditioning agents is included in the composition of the present invention, preferably in an amount of about 0.5% to about 3% by total weight of the composition, the composition also can include a suspending agent for the conditioning agent, in an amount of about 0.5% to about 5%, by total weight of the composition. Such suspending agents also may be useful for suspending solvent-insoluble oligomers. The particular suspending agent is not critical and can be selected from any materials known to suspend water or solvent-insoluble liquids in shampoo compositions. Suitable suspending agents are for example, distearyl amate (distearyl phthalamic acid); fatty acid alkanolamides; esters of polyols and sugars; polyethylene glycols; the ethoxylated or propoxylated alkylphenols; ethoxylated or propoxylated fatty alcohols; and the condensation products of ethylene oxide with long chain amides. These suspending agents, as well as numerous others not cited herein, are well known in the art and are fully described in the literature, such as McCUTCHEON'S DETERGENTS AND EMULSIFIERS, 1989 Annual, published by McCutcheon Division, MC Publishing Co.

A nonionic, water-soluble alkanolamide also is optionally included preferably in an amount of about 0.1% to about 3% by weight in the styling aid compositions that include a conditioning agent to provide exceptionally stable emulsification of water-insoluble conditioning agents and to aid in thickening. Suitable water-soluble alkanolamides include, but are not limited to, those known in the art of hair care formulations, such as cocamide monoethanolamide (MEA), cocamide diethanolamide (DEA), soyamide DEA, lauramide DEA, oleamide monoisopropylamide (MIPA), stearamide MEA, myristamide MEA, lauramide MEA, capramide DEA, ricinoleamide DEA, myristamide DEA, stearamide DEA, oleylamide DEA, tallowamide DEA, lauramide MIPA, tallowamide MEA, isostearamide DEA, isostearamide MEA and combinations thereof. Other suitable suspending agents are disclosed in Oh et al. U.S. Pat. No. 4,704,272; Grote et al. U.S. Pat. No. 4,741,855; and Bolich, Jr. et al. U.S. Pat. No. 4,788,006, which patents are hereby incorporated by reference.

Emulsion stabilizers also may be used in compositions of the invention. Useful examples include, such compounds as polyethylene glycol, silicone copolyols, polyvinyl alcohol, sorbitan monostearate, oleth-2, sorbitan monolaurate, and nonionic block copolymers of ethylene oxide and propylene oxide such as those marketed by BASF Wyandotte under the name PLURONICS ®. When present, such stabilizers comprise from about 0.05% to about 1%, preferably from about 0.1% to about 0.8%, by weight of the composition.

The propellant gas included in the aerosol mousse forms of the compositions of the present invention can be any liquifiable gas conventionally used for aerosol mousse containers. Examples of materials that are suitable for use as propellants are dimethyl ether, propane, n-butane and isobutane, and other water-soluble hydrocarbon gases used singly or admixed. Water-soluble gases such as dimethyl ether, carbon dioxide, and/or nitrous oxide also can be used to obtain aerosols having reduced flammability.

Other insoluble, compressed gases such as nitrogen, helium and fully-fluorinated oxetanes and oxepanes also are useful to deliver the compositions from aerosol containers.

The amount of the propellant gas is governed by normal factors well known in the aerosol mousse art. For mousses, the level of propellant is generally from about 3% to about 30%, preferably from about 5% to about 15% of the total composition. If a propellant such as dimethyl ether utilizes a vapor pressure suppressant (e.g., trichlorethane or dichloromethane), for weight percentage calculations, the amount of suppressant is included as part of the propellant.

Other common cosmetic additives can be incorporated with the essential ingredients of the present invention, as long as the capability of polymerizing the oligomers in-situ is not adversely affected. These additives include, but are not limited to, commonly used fragrances, dyes, opacifiers, pearlescing agents, preservatives, water softening agents, acids, bases, sequestering agents, buffers and the like; and will usually be present in weight percentages of less than about 1% each, and about 2% to about 5% in total. Suitable solvents include the lower alcohols like ethanol and isopropanol; polyols like glycerol; glycols or glycol ethers, like 2-butoxyethanol, ethylene glycol, ethylene glycol monoethyl ether, propylene glycol and diethylene glycol monomethyl ether; and mixtures thereof. These solvents can be present in the hair setting composition of the present invention in an amount from about 1% to about 99.5% by weight.

The compositions can be thickened, for example, with, in addition to the alkanolamides described above, sodium alginate, guar gum, xanthan gum, gum arabic, cellulose derivatives such as methylcellulose, hydroxybutylcellulose, hydroxyethylcellulose, hydroxypropylcellulose and carboxymethylcellulose, and various polymeric thickeners, such as acrylic acid derivatives. It is also possible to use inorganic thickeners such as bentonite. These thickeners are preferably present in the amount from about 0.1% to about 10% by weight and, in particular, from about 0.5% to about 3% by weight, relative to the total weight of the composition.

The compositions also can include anionic, amphoteric or nonionic surfactants, to impart cleansing and/or emulsifying properties to the composition. Likewise, the compositions can contain other emulsifiers, fatty alcohols, humectants, cationic surfactants, such as cetrimonium chloride, and similar materials to provide conditioning properties, aesthetic properties and desirable physical properties to the composition.

For example, representative nonionic surfactants include esters or polyols and sugars; the polyethoxylated and/or polypropoxylated alkylphenols; the polyhydroxylated polyethers of fatty alcohols; and the condensation products of ethylene oxide with long chain mercaptans or long chain amides. Similarly, representative anionic surfactants include alkali metal salts, ammonium salts or salts of amines or amino alcohols of fatty acids such as oleic acid; of the sulfates of fatty alcohols, principally $C_{12}$–$C_{14}$ and $C_{16}$ fatty alcohols; of the sulfates of polyethoxylated fatty alcohols; the alkylbenzenesulfonates, such as those wherein the alkyl moiety has about 12 to about 22 carbon atoms; or the alkylarylpolyether sulfates and monoglyceride sulfates. All these nonionic and anionic surfactants, as well as numerous others not cited here, are well known in the art and are fully described in the literature.

The alcohol solvent that may be employed in the composition preferably is an aliphatic straight or branched chain monohydric alcohol having 2 to about 4 carbon atoms. Isopropanol and especially ethanol are preferred. The concentration of the alcohol in the composition can be from about 3% to about 99.5% by weight, preferably about 5% to about 50% by weight and more preferably about 5% to about 25% by weight.

Where oligomer precipitation in the composition occurs at a higher alcohol and/or glycol percentage, compatible suspending stabilizing agents can be included. The polymer solutions/dispersions are stable at a pH value between 1 and 12, although a pH value between 3 and 9 are desired in personal care products. A number of adjuvants such as surfactants, emollients, silicones, monovalent mineral salts fragrance, can be added as desired.

EXPERIMENTAL

Preparation of In-situ Hydrophobic Polyurethane-Acrylate Hair Bodifying and Set Retention Polymer Five grams of a urethane-acrylate oligomer is mixed with 6 grams of ethanol and 1 gram of octyl dimethyl p-aminobenzoic acid (UV light absorber) in a first composition and the mixture is shaken vigorously. In a second composition, 0.4 gram (78% active) benzoyl peroxide (ground powder) and 14.8 grams of ethanol were mixed as a polymerization initiator. The two compositions are combined as a mixed solution using 7.6 grams of the first composition and 2.4 grams of the second composition immediately prior to application to rolled hair tresses. The hair tresses are dipped into the mixed solution and then the tresses are heated at about 40° C. for about 45 minutes in an oven in a weight ratio of the composition to hair of 1:1. Some tresses are pretreated with a spray of 10.5 pH NH$_4$OH. The bulk volume of the hair (bodifying) is substantially increased with and without the pretreatment. After washing, the body of the hair remained substantially increased and remained soft.

EXAMPLE 1

ANHYDROUS FORMULATION

| | WEIGHT % |
|---|---|
| PHASE A | |
| URETHANE-ACRYLATE OLIGOMER | 10.0 |
| REAGENT ALCOHOL | 12.0 |
| OCTYL DIMETHYL PABA (ESCALOL 507) | 2.0 |
| PHASE B | |
| BENZOYL PEROXIDE (78%) (CADET BPO-78) | 2.0 |
| REAGENT ALCOHOL | 74.0 |
| PRECEDURE: | Dissolve all components in Phase A in a vial by simple stirring. Best to add oligomer to alcohol-PABA mixture. Weigh benzoyl peroxide and place into a glass mortar. Grind benzoyl peroxide with ethanol to disperse. Add Phase B to Phase A and shake vial. |

PRECEDURE: Dissolve all components in Phase A in a vial by simple stirring. Best to add oligomer to alcohol-PABA mixture. Weigh benzoyl peroxide and place into a glass mortar. Grind benzoyl peroxide with ethanol to disperse. Add Phase B to Phase A and shake vial.

What is claimed is:

1. A method of treating human hair for increased polymer durability comprising:

applying to said hair an oligomeric compound formed by end capping a urethane oligomer with a bisulfite or an acrylate group, wherein the oligomer has a degree of polymerization in the range of about 2 to 200, and contains no free isocyanate; and polymerizing the oligomer while said oligomer is in contact with said hair to form, in-situ, a polymer adhered to said hair.

2. A method as defined in claim 1, wherein the oligomeric compound is a urethane-acrylate.

3. A method as defined in claim 2, wherein the urethane is formed from a polyfunctional hydroxyl compound and an aliphatic diisocyanate.

4. A method as defined in claim 2, wherein the oligomeric compound is a urethane oligomer end capped with a hydroxyl-containing acrylate monomer.

5. A method as defined in claim 1, wherein the oligomer is a polycarbamoyl sulfonate formed by end capping a urethane oligomer with a bisulfite moiety.

6. A method as defined in claim 11 further including another oligomer selected from the group consisting of a polyurethane; a poly(urethaneacrylate); a polyacrylic oligomer and a self-crosslinking polyacrylate.

7. A method as defined in claim 1 further including the step of adding a reaction initiator to the composition in an amount of about 0% to about 5% by weight of the composition.

8. A method as defined in claim 7, wherein the initiator is a compound selected from the group consisting of peroxo, diazo, sulfite, bisulfite, persulfate and mixtures thereof.

9. A method as defined in claim 8 further including adding a chain transfer agent in an amount of about 0.1% to about 5% by weight of the oligomer(s) in the composition.

10. A method as defined in claim 8, wherein the chain transfer agent is selected from the group consisting of isopropyl alcohol, an alkylmercaptan, and mixtures thereof.

11. A method as defined in claim 1 further including adding an ionizable metal salt in an amount of about 0.1% to about 10% of the weight of oligomers in the composition wherein the metal has a valence of at least II, for in-situ crosslinking of the oligomer, and wherein the composition has a pH above about 7.0.

12. A method of treating human hair for increased polymer durability comprising:

applying to said hair an oligomeric compound formed by end capping a urethane oligomer with an acrylate group, wherein the oligomer has a degree of polymerization in the range of about 2 to 200, and contains no free isocyanate; and polymerizing the oligomer while said oligomer is in contact with said hair to form, in-situ, a polymer adhered to said hair.

13. A method as defined in claim 12, wherein the urethane oligomer is formed from a polyfunctional hydroxyl compound and an aliphatic diisocyanate.

14. A method as defined in claim 12, wherein the oligomeric compound is a urethane oligomer end capped with a hydroxyl-containing acrylate monomer.

15. A method as defined in claim 12 further including the step of adding a reaction initiator to the composition in an amount of about 0.1% to about 10% of the weight of the oligomers in the composition.

16. A method as defined in claim 15, wherein the reaction initiator is included in an amount of about 0.5% to about 5% of the weight of the oligomers in the composition.

17. A method as defined in claim 15, wherein the initiator is a compound selected from the group consisting of peroxo, diazo, sulfite, bisulfite, persulfate and mixtures thereof.

18. A method as defined in claim 12 further including adding a chain transfer agent in an amount of about 0.1% to about 5% by weight of the oligomer(s) in the composition.

19. A method as defined in claim 18, wherein the chain transfer agent is selected from the group consisting of isopropyl alcohol, an alkylmercaptan, and mixtures thereof.

20. A method as defined in claim 12 further including adding an ionizable metal salt in an amount of about 0.1% to about 10% of the weight of oligomers in the composition wherein the metal has a valence of at least II, for in-situ crosslinking of the oligomer, and wherein the composition has a pH above about 7.0.

* * * * *

UNITED STATES PATENT AND TRADEMARK OFFICE
CERTIFICATE OF CORRECTION

PATENT NO.  : 5,362,486
DATED       : November 8, 1994
INVENTOR(S) : Nandagiri, et al It is certified that error appears in the above-indentified patent and that said Letters Patent is hereby corrected as shown below:

Column 3, line 38, after "No." delete "4,682,616" and substitute therefor -- 4,682,612 --;

Column 8, line 61, after "about" delete "0,001" and substitute therefor -- 0.001 --;

Column 9, line 10, delete -- incuding -- and substitute therefor -- including --; and Column 15, lines 57-62,      'PRECEDURE: Dissolve all components in Phase A in a vial by simple stirring. Best to add oligomer to alcohol-PABA mixture. Weigh benzoyl peroxide and place into a glass mortar. Grind benzoyl peroxide with ethanol to disperse. Add Phase B to Phase A and shake vial. --

Column 15, line 50, "Precedure" should read --Procedure --.

Signed and Sealed this

Fourth Day of April, 1995

Attest:

BRUCE LEHMAN

*Attesting Officer*          *Commissioner of Patents and Trademarks*

UNITED STATES PATENT AND TRADEMARK OFFICE
CERTIFICATE OF CORRECTION

PATENT NO. : 5,362,486
DATED : November 8, 1994
INVENTOR(S) : Nandagiri, et al

It is certified that error appears in the above-indentified patent and that said Letters Patent is hereby corrected as shown below:

Column 3, line 38, after "No." delete "4,682,616" and substitute therefor -- 4,682,612 --;

Column 8, line 61, after "about" delete "0,001" and substitute therefor -- 0.001 --;

Column 9, line 10, delete -- incuding -- and substitute therefor -- including --; and Column 15, lines 57-62, should be deleted.

Column 15, line 50, "Precedure" should read --Procedure --.

This certificate supersedes Certificate of Correction issued April 4, 1995.

Signed and Sealed this

Thirteenth Day of June, 1995

Attest:

BRUCE LEHMAN

Attesting Officer     *Commissioner of Patents and Trademarks*